US012599686B2

(12) United States Patent
Baum et al.

(10) Patent No.: US 12,599,686 B2
(45) Date of Patent: Apr. 14, 2026

(54) STERILIZATION CASE FOR SURGICAL DEVICE

(71) Applicant: BING3IDEAS, LLC, Tustin, CA (US)

(72) Inventors: Douglas D. Baum, Santa Ana, CA (US); Jeffrey D. Corless, Santa Ana, CA (US); Raymond V. Schnell, Tustin, CA (US)

(73) Assignee: BING3IDEAS, LLC, Tustin, CA (US)

( * ) Notice: Subject to any disclaimer, the term of this patent is extended or adjusted under 35 U.S.C. 154(b) by 528 days.

(21) Appl. No.: 18/070,150

(22) Filed: Nov. 28, 2022

(65) Prior Publication Data

US 2023/0158186 A1    May 25, 2023

Related U.S. Application Data

(63) Continuation of application No. PCT/US2021/033429, filed on May 20, 2021.

(60) Provisional application No. 63/031,140, filed on May 28, 2020.

(51) Int. Cl.
| | |
|---|---|
| *A61L 2/10* | (2006.01) |
| *A61B 50/30* | (2016.01) |
| *A61L 2/26* | (2006.01) |
| *B65D 25/10* | (2006.01) |
| *B65D 43/16* | (2006.01) |

(52) U.S. Cl.
CPC ............... *A61L 2/10* (2013.01); *A61B 50/30* (2016.02); *A61L 2/26* (2013.01); *B65D 25/108* (2013.01); *B65D 43/163* (2013.01); *A61L 2202/11* (2013.01); *A61L 2202/121* (2013.01); *A61L 2202/122* (2013.01); *A61L 2202/24* (2013.01); *B65D 2213/00* (2013.01); *B65D 2543/00574* (2013.01)

(58) Field of Classification Search
CPC .............. A61L 2/10; A61L 2/26; A61B 50/30
See application file for complete search history.

(56) References Cited

U.S. PATENT DOCUMENTS

| | | |
|---|---|---|
| 10,549,001 B2 | 2/2020 | Martz et al. |
| 2005/0238530 A1 | 10/2005 | Frieze et al. |
| 2019/0250395 A1 | 8/2019 | Ishimoda |

OTHER PUBLICATIONS

WO PCT/US21/33429 ISR and Written Opinion, Feb. 21, 2021.

*Primary Examiner* — Sean E Conley
(74) *Attorney, Agent, or Firm* — ONE LLP

(57) ABSTRACT

The present disclosure is related to a self-contained medical grade case for sterilizing surgical devices, for example surgical loupes, utilizing UV-C germicidal light while also protecting the surgical devices from damage. In some embodiments, the case can thus ensure patient safety and prevent cross contamination.

19 Claims, 6 Drawing Sheets

STERILIZATION CASE FOR SURGICAL DEVICE

CROSS-REFERENCE TO RELATED APPLICATIONS

The present application is a continuation of International Patent Application No. PCT/US21/33429, filed May 20, 2021, which claims priority to U.S. Provisional Patent Application No. 63/031,140, filed May 28, 2020, both of which are incorporated herein by reference in their entireties.

FIELD his disclosure relates generally to the field of device sterilization, and more particularly, to sterilization for surgical loupes.

BACKGROUND

The background includes information that may be useful in understanding the present disclosure. It is not an admission that any of the information provided herein is prior art or relevant to the presently claimed invention, or that any publication specifically or implicitly referenced is prior art.

Surgical loupes are magnifying glasses that dentists, surgeons, and other healthcare professionals wear to magnify the area of interest on a patient. For example, in dental/medical applications, loupes may be worn to magnify the surgical field. Loupes are also worn to allow a more "physiologic" posture while working, and thereby minimize the slouching that may otherwise develop. An example pair of surgical loupes worn by surgeons is shown in FIG. 1.

Given their use in medical/dental applications, where exposure to patient aerosols and/or bodily fluids that contain pathogens is extremely prevalent, loupes should be sterilized after each use to ensure both patient and user safety. Loupes are often highly customized and constructed from expensive, delicate optical materials that require the use of special cleaning solutions/wipes that do have a corrosive effect on the loupes' components. These solutions do not contain a high enough proportion of isopropyl alcohol to adequately sterilize the loupes and therefore increase the risk of cross-contamination.

In addition, the loupes' design makes it difficult to sterilize every surface and crevice by hand with a wipe. This process consumes considerable user productivity and valuable time healthcare professionals could spend with their patients.

Therefore, there is a need to provide a device to sterilize loupes using ultraviolet germicidal irradiation that uses short wavelength at 254-265 nm (ultraviolet C or UV-C) for more effective sterilization that exposes the entire surface of the loupes to the sterilization properties of UV-C.

SUMMARY

Provided herein are example embodiments of systems, devices, and methods for a self-contained medical grade case for sterilizing and protecting surgical devices, for example surgical loupes, utilizing UV-C germicidal light, while also protecting the surgical devices from damage. The case can thus ensure clinician and patient safety, as well as prevent cross contamination.

Generally, the present disclosure can include a case comprised of a crush-resistant housing having an upper portion and a lower portion, wherein the upper portion and the lower portion are joined when the housing is in the closed position; the lower portion further comprising a compartment, the compartment comprises: one or more array of UV-C light emitting diodes, a battery power source electrically coupled to the plurality of UV-C light emitting diodes, a loupe rest assembly, a cable management assembly with integrated cavity to house a tracking device (e.g., a Bluetooth tracking device), an inner wall assembly to secure the external battery that powers loupe light, a USBC charging port to recharge loupe light battery; a hinge assembly for joining the upper portion and the lower portion; and a safety mechanism for allowing the battery source to power the array of UV-C light emitting diodes only when the housing is in the closed position.

Other compositions, variations, methods, features and advantages of the subject matter described herein will be or will become apparent upon examination of the following detailed description. It is intended that all such additional compositions, variations, methods, features, and advantages be included within this description, be within the scope of the subject matter described herein, and be protected by the accompanying claims. In no way should the features of the example embodiment be construed as limiting the appended claims, absent express recitation those features in the claim.

BRIEF DESCRIPTION OF THE FIGURES

The following drawings form part of the present specification and are included to further illustrate aspects of the present disclosure. A more particular description of the embodiments briefly described above will be rendered by reference to specific embodiments thereof, which are illustrated in the accompanying drawings. It should be noted that the components in the figures are not necessarily to scale, emphasis instead being placed upon illustrating the principles of the disclosure. Moreover, in the figures, like reference numerals designate corresponding parts throughout the different views. However, like parts do not always have like reference numerals. Moreover, all illustrations are intended to convey concepts, where relative sizes, shapes and other detailed attributes may be illustrated schematically rather than literally or precisely.

DETAILED DESCRIPTION

Figure 1:
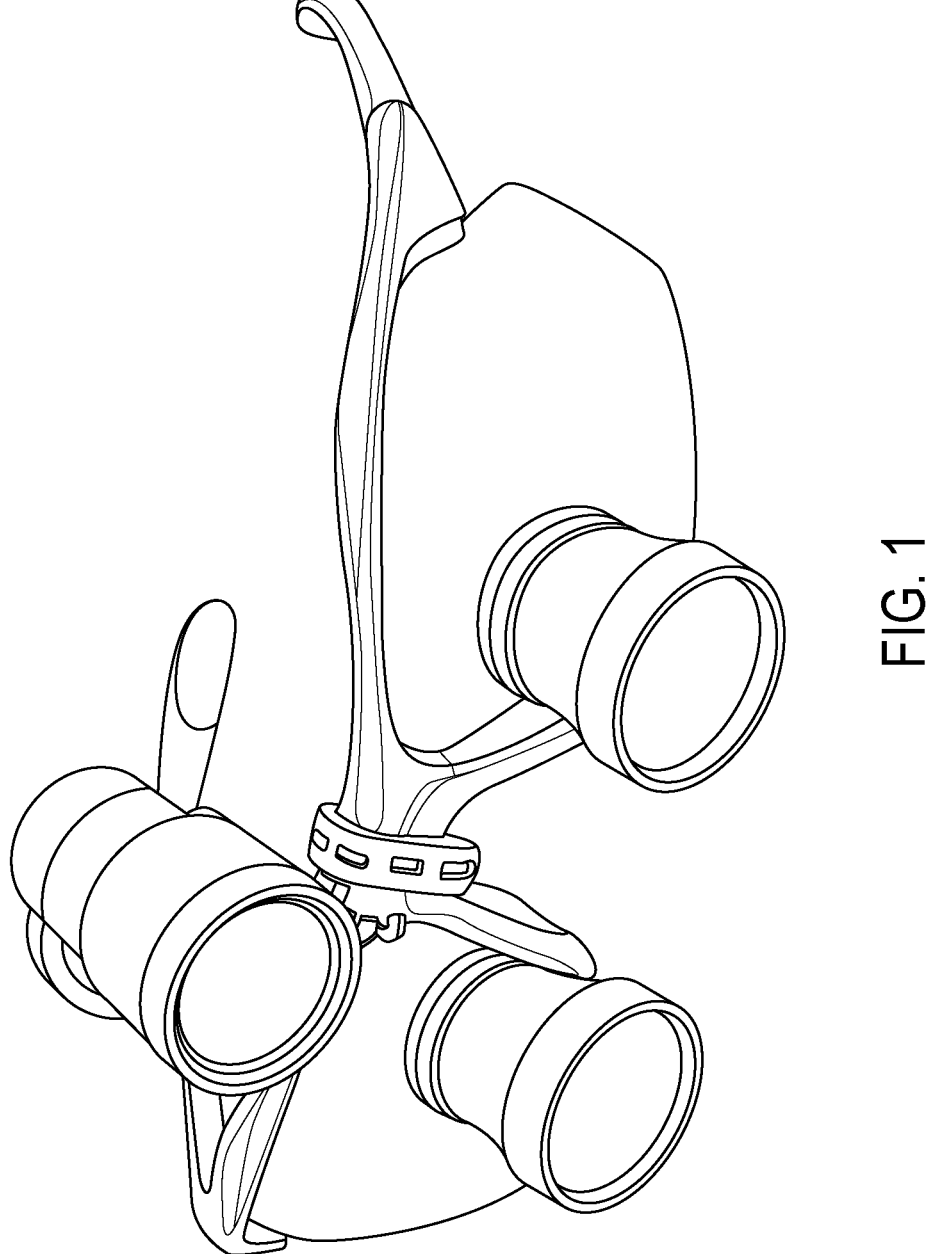
FIG. 1 is exemplary pair of surgical loupes.

Before the present subject matter is described in detail, it is to be understood that this disclosure is not limited to the particular embodiments described herein, as such may, of course, vary. It is also to be understood that the terminology used herein is for the purpose of describing particular embodiments only, and is not intended to be limiting, since the scope of the present disclosure will be limited only by the appended claims.

As used herein and in the appended claims, the singular forms "a," "an," and "the" include plural referents unless the context clearly dictates otherwise.

While the embodiments are susceptible to various modifications and alternative forms, specific examples herein are shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

As used herein and in the appended claims, the singular forms "a," "an," and "the" include plural referents unless the context clearly dictates otherwise.

In general, terms such as "coupled to," and "configured for coupling to," and "secure to," and "configured for securing to" and "in communication with" (for example, a first component is "coupled to" or "is configured for coupling to" or is "configured for securing to" or is "in communication with" a second component) are used herein to indicate a structural, functional, mechanical, electrical, signal, optical, magnetic, electromagnetic, ionic or fluidic relationship between two or more components or elements. As such, the fact that one component is said to be in communication with a second component is not intended to exclude the possibility that additional components may be present between, and/or operatively associated or engaged with, the first and second components.

In the above description and in the figures, like elements are identified with like reference numerals. The use of "e.g.," "etc.," and "or" indicates non-exclusive alternatives without limitation, unless otherwise noted. The use of "including" or "includes" means "including, but not limited to," or "includes, but not limited to," unless otherwise noted.

As used herein, the term "and/or" placed between a first entity and a second entity means one of (1) the first entity, (2) the second entity, and (3) the first entity and the second entity. Multiple entities listed with "and/or" should be construed in the same manner, i.e., "one or more" of the entities so conjoined. Other entities may optionally be present other than the entities specifically identified by the "and/or" clause, whether related or unrelated to those entities specifically identified. Thus, as a non-limiting example, a reference to "A and/or B," when used in conjunction with open-ended language such as "comprising" can refer, in one embodiment, to A only (optionally including entities other than B); in another embodiment, to B only (optionally including entities other than A); in yet another embodiment, to both A and B (optionally including other entities). These entities may refer to elements, actions, structures, steps, operations, values, and the like.

Generally, embodiments of the present disclosure include systems, devices, and methods for a self-contained medical grade case for sterilizing and protecting surgical devices, for example surgical loupes, utilizing UV-C germicidal light, for example at a wavelength of 254-265 nm, while also protecting the surgical devices from physical damage. The UC-V light can have a germicidal kill rate of a 99+%. The case can thus ensure clinician and patient safety, as well as prevent cross contamination.

Figures 2A, 2B:
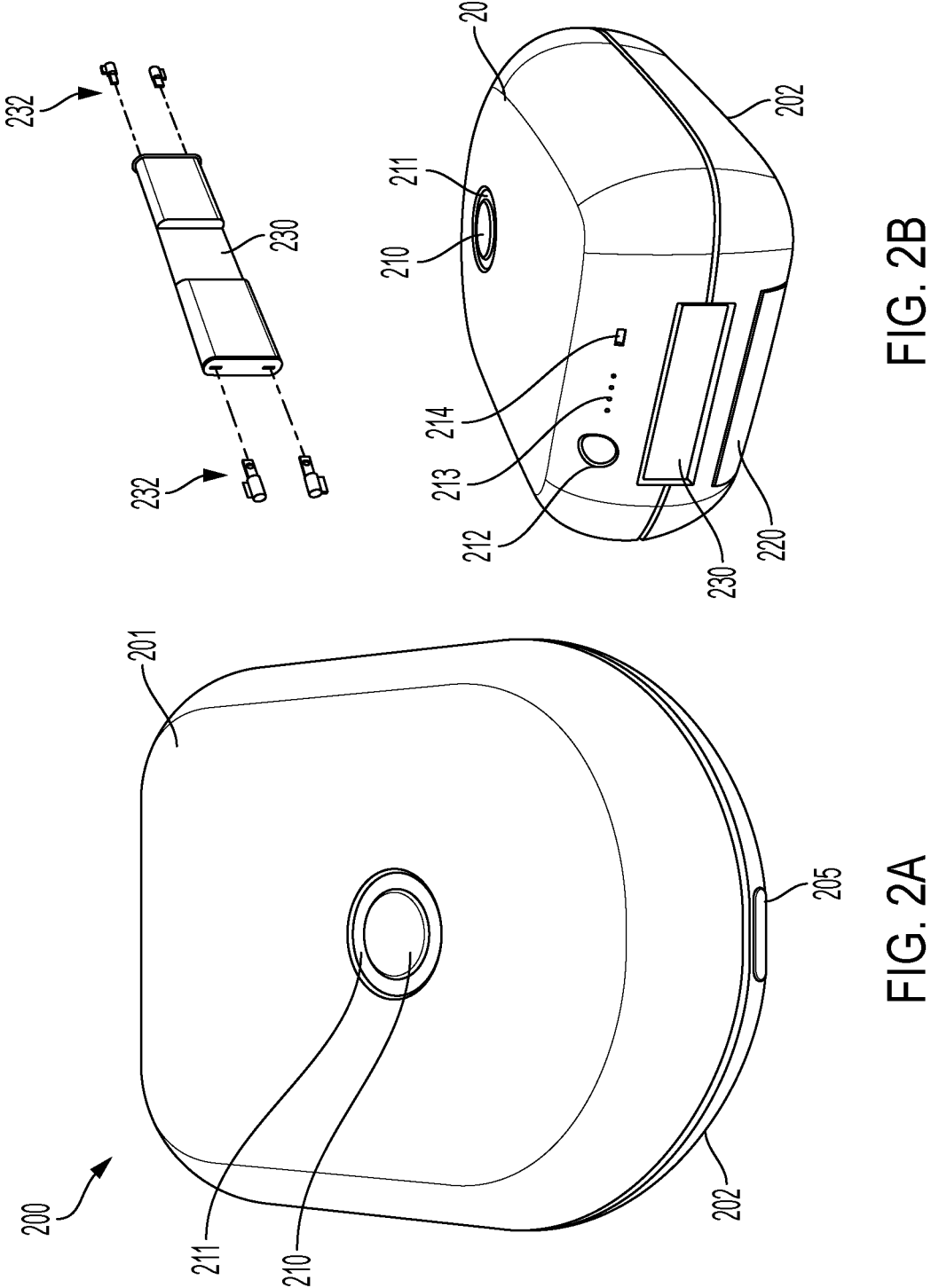
FIG. 2A shows an exemplary perspective front and top view of a case of the present disclosure.
FIG. 2B shows an exemplary perspective back and top view of a case of the present disclosure.

Turning now to the drawings, FIG. 2A shows an exemplary perspective front and top view of a case 200 of the present disclosure. The case 200 can include a body (or housing) which includes a top portion (which may be referred to as a lid) 201 and a bottom portion 202. In some embodiments, the top portion 201 can include button 210 and ring 211. The button 210 can be activated (pushed down by a user) to start a sterilization cycle. In some embodiments, the ring 211 can be or can include a light. During the duration of the sterilization cycle, the ring 211 can light up such that it resembles a light swirling or circling along (around) the ring 211. When the sterilization cycle completes, the light can stop swirling and stay constant. In some embodiments, the sterilization cycle can take approximately 90 seconds. The case can also include a latch button 205, which when pushed can allow the top portion 201 to disengage from the bottom portion 202, to open the case 200. When the case is opened, the light ring 211 can turn off.

In some embodiments, the body of the case 200, which includes the top portion 201 and bottom portion 202 can be made of crush-resistant material to protect the loupe and its components placed inside the case.

FIG. 2B shows an exemplary perspective back and top view of a case 200 of the present disclosure. As shown, the case can include a power button 212, a charging status light array 213, and a charging port 214. The charging light array 213 can indicate the progress of charging. For example, when the first (of four) light blinks, it indicates the battery is less than 25% charged and the battery is charging; then the first solid light indicates the battery is 25% charged; when the second light blinks, it indicates the battery is less than 50% charged and the battery is charging; then the second solid lights indicate the battery is 50% charged, and so on. In some embodiments, the charging port 214 can be a USB/USB-C port.

Figures 7A, 7B:
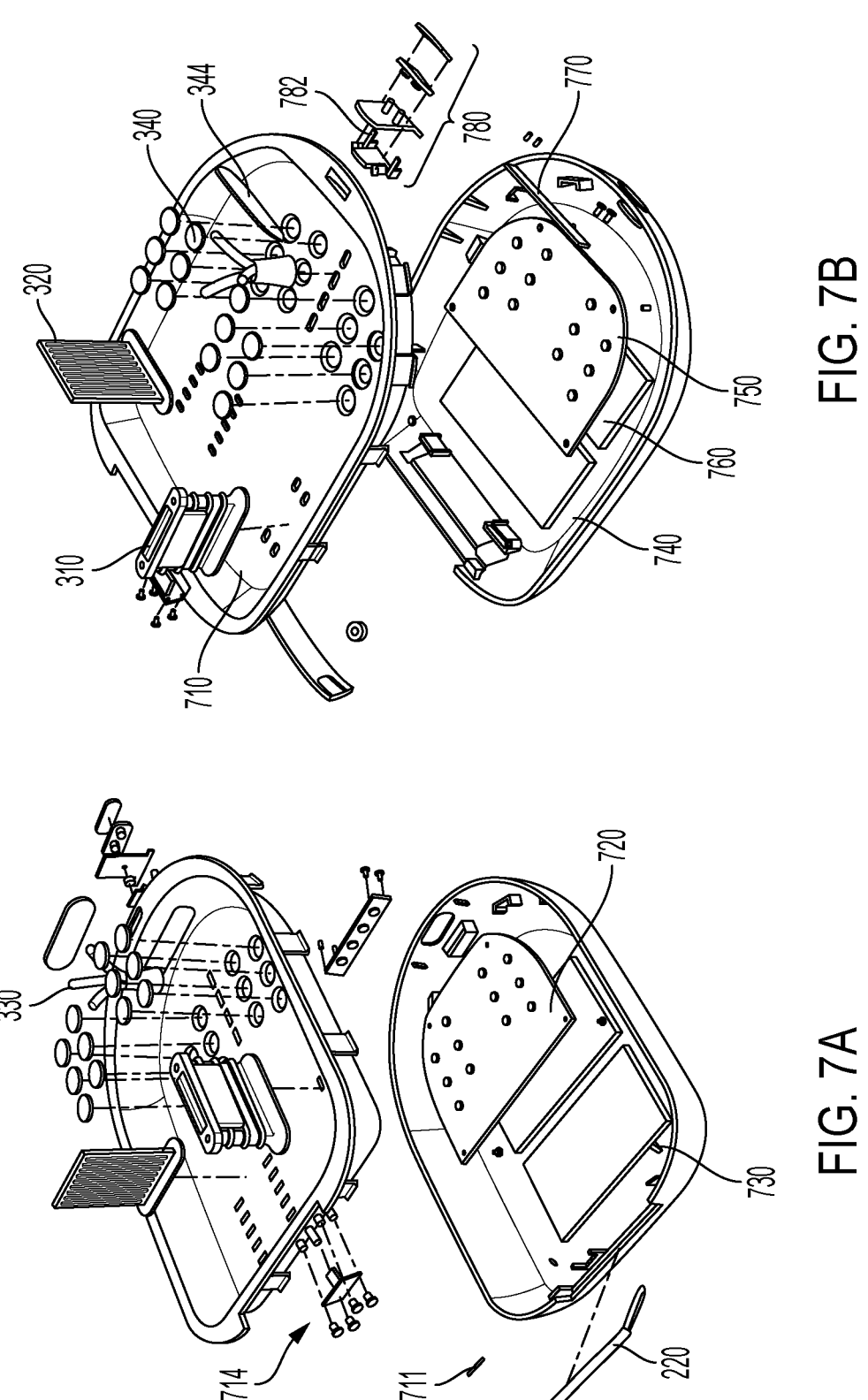
FIGS. 7A and 7B show exemplary exploded views of the bottom portion of the present disclosure.

FIG. 2B further shows an exemplary handle 220 (also shown in FIGS. 7A and 7B). In some embodiments, the handle 220 can retract into a recess. In some implementations, the handle 220 can be made of rubber. The case can include a hinge 230 (and hinge components 232) as an attachment mechanism to attach the top portion 201 with the bottom portion 202.

Figures 3A, 3B:
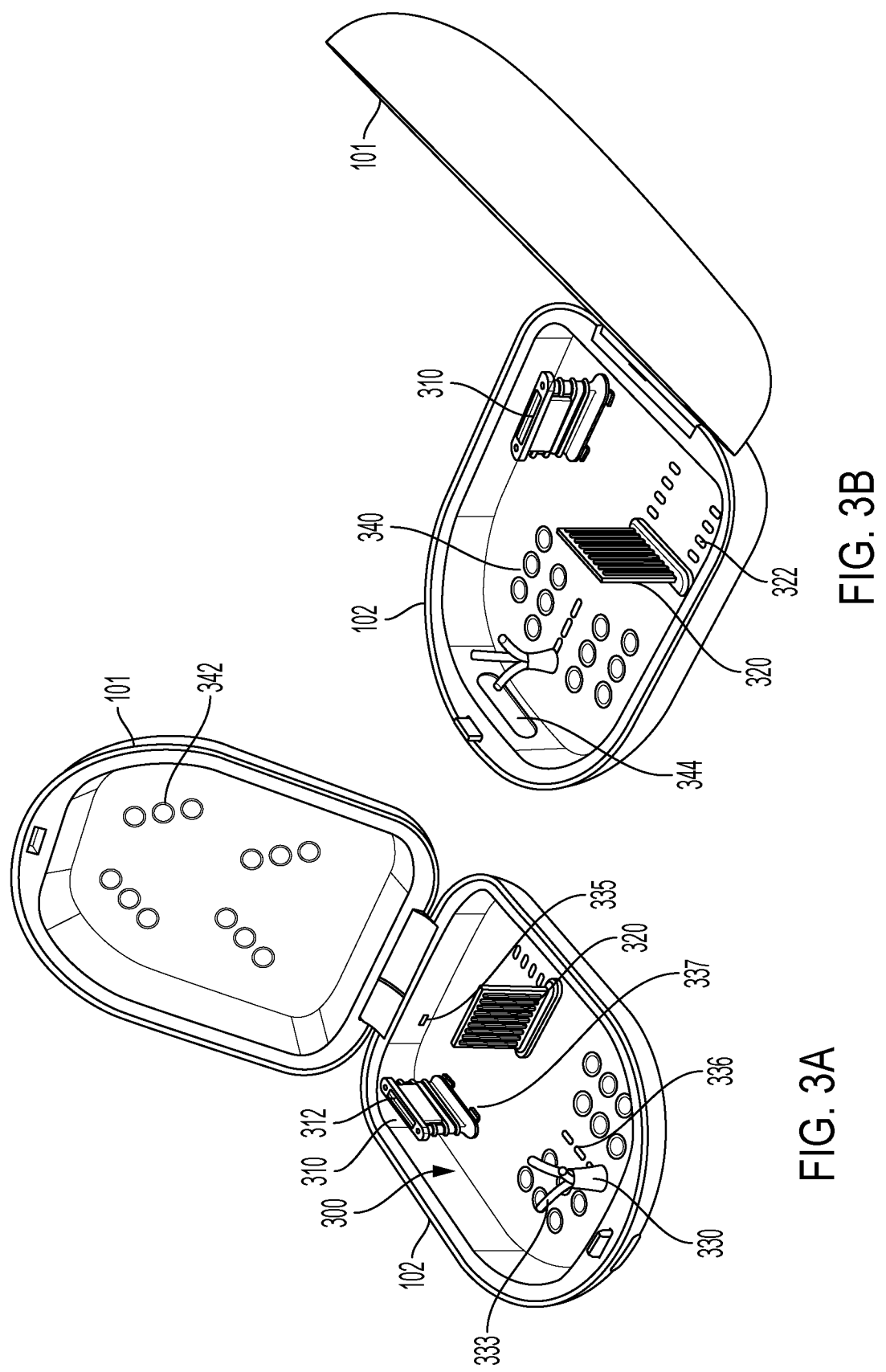
FIGS. 3A and 3B show an exemplary internal compartment of a case of the present disclosure.
Figure 4:
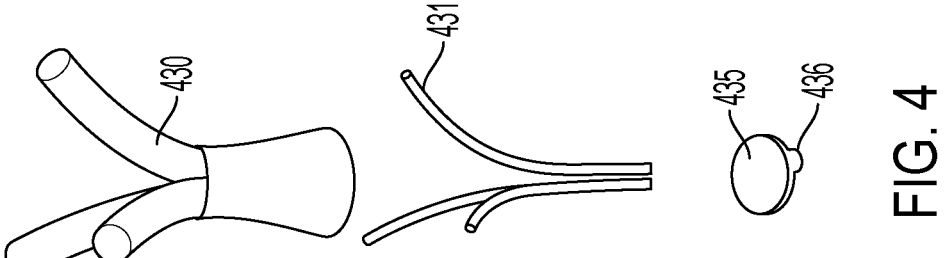
FIG. 4 shows an exemplary exploded view of a loupe rest assembly of the present disclosure.

FIGS. 3A and 3B show an exemplary internal compartment of the case 200. In some embodiments, the bottom portion 102 can include an internal compartment 300 which can receive and store a surgical loupe and related components. For example, the compartment 300 can include a cable management assembly 310, an inner wall 320, and a loupe rest assembly 330. The loupe rest assembly 330 (also shown in FIG. 4) can include a plurality of loupe rest assembly arms 333, which can hold a surgical loupe. In some embodiments, as shown in FIG. 4, the loupe rest assembly 330 can include bendable (or foldable) wires 431 which are covered by over-mold 430. In some exemplary operations, a loupe (e.g., a nose bridge of the loupe) can be placed into the arms 333, and the wires 431 can be bent so as to restrict the movement of the loupe, and thus can hold the loupe in a secure position.

Figure 6:
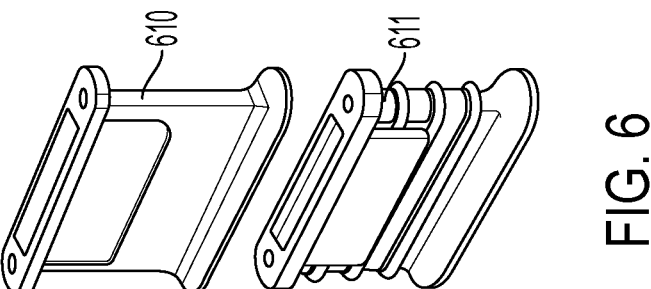
FIG. 6 shows an exemplary exploded view of a cable management assembly of the present disclosure.
Figure 5:
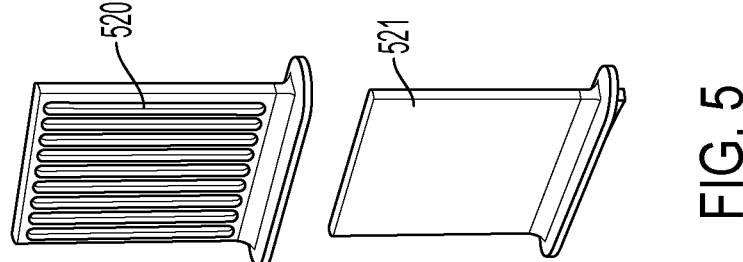
FIG. 5 shows an exemplary exploded view of an inner wall of the present disclosure.

The cable management assembly 310 can receive a cable of the loupe. For example, the cable can be wrap around the cable management 310 and terminate a male end of the battery cable into a female receptacle of the cable management assembly 310. In some embodiments, as shown in FIG. 6, the cable management assembly 310 can include a body 610 and an over-mold 611. The over-mold 611 can include one or more grooves to receive the cable. In some embodiments, the top end of the cable management assembly 310 can include an opening 312. The opening 312 can receive, for example, a wireless tile tracking device (e.g., a Bluetooth tracking device), AirTag™, or the like. The tile can be used to track the location of the case.

As shown further, the compartment 300 can include a plurality of transparent covers 340 on the bottom surface and a cover 344 on the front inside wall. The transparent covers cover light emitting diodes (LED) UV-C lights which can shine through them. The inside surface of the top portion 101 can also include a plurality of covers 342 through which LED (UV-C) lights can shine. In some embodiments, the covers may be made of quartz crystal. In some exemplary operations, the front of a loupe can be placed facing the cover 344, thus the LED lights behind the cover 344 can sterilize the front of the loupe. In some embodiments, the cover 344 can have an oblong shape and four LED lights can be included behind the cover 344.

The compartment 300 can also include a charging port 335, e.g., USB-C port. The charging port 335 can charge a battery placed in the compartment 300, for example, a battery for the light of the loupe. The inner wall 320 can hold the battery and a clip (e.g., clip used with loupe battery cable). In some implementations, the charging port may not operate (not charging) during a sterilization cycle.

In some embodiments, the bottom surface of the compartment 300 can include slots 322, 336, and 337. The slots 322, 336 and 337 can allow the inner wall 320, the loupe rest assembly 330 and the cable management assembly 310, respectively, to be repositioned, e.g., toward the front, back or side of the compartment 300. The repositioning can be used, for example, to accommodate the sizes of the loupe and the battery. As shown in FIG. 4, the bottom end of the loupe rest assembly 330 can include a plug 435 with an extruding stud 436 which can securely fit into slots 336. The bottom end of the inner wall 320 and cable management system 310 can include similar studs that fit into slots 322 and 337.

FIGS. 7A and 7B show exemplary exploded views of the bottom portion 102. In some embodiments, the bottom portion can include a fabric 710 (which can be a reflective fabric). The top surface of the fabric 710 can receive the cable management assembly 310, the inner wall 320, and the loupe rest assembly 330 as shown above. The fabric 710 can serve to separate, protect or hide components including, for example, one or more battery 760, a LED PCBA 750, a front LED PCB 770, etc. In some embodiments, battery 760 can provide power to all electric and electronic components of the case 200, as well as power to the USB-C charging port 335. As shown further in FIG. 7B, a latch assembly 780 with latch components 782 (e.g., latch springs, button, etc.) can be located between the fabric 710 and the outer shell of the bottom portion 102. Also shown are various washers used, for example, washer 711 for the handle 220, and 720 for screws 730 for the LED PCBA 750. As shown, the LED PCBA 750 can include one or more array of LED lights. The LED PCB 770 can include front LED lights.

In some embodiments, the case 200 can include a safety mechanism. For example, the safety mechanism can only allow a sterilization cycle to start only when the case 200 is in a closed position. In some embodiments, the safety mechanism can be or can include the latch assembly 780.

FIG. 7A also shows a PCB 714 which can include the USB-C port 214 (FIG. 2).

Figure 8B:
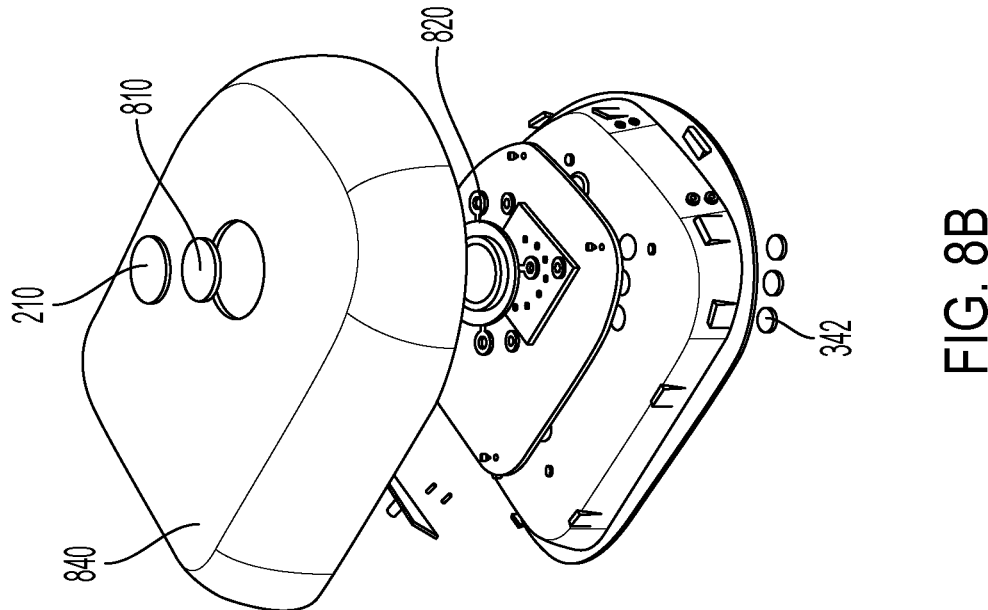
FIGS. 8A and 8B show exemplary exploded views of the top portion of the present disclosure.
Figure 8A:
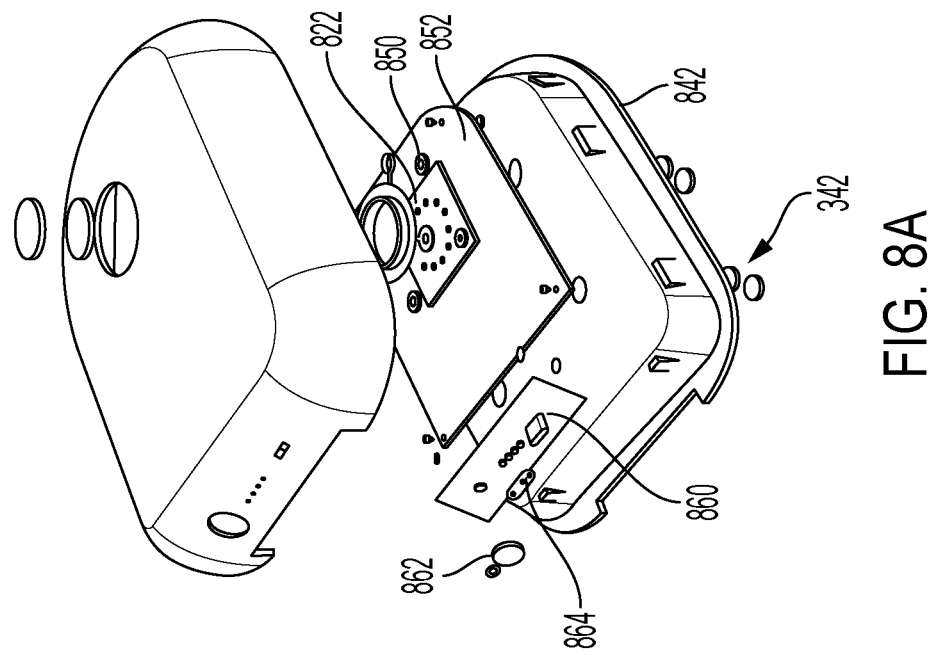

FIGS. 8A and 8B show exemplary exploded views of the top portion 101. As with the bottom portion, the top portion can also include a a fabric 842 (which can be a reflective fabric). The fabric 842 can serve to separate, protect or hide components including, for example, a LED PCBA 852, one or more LED lights 822, light ring cover 820, etc.

In some exemplary operations, the lights 822 can turn on and off sequentially in a circle formation, thus giving an effect of a swirling light motion. This swirling motion can occur during a sterilization cycle. When the sterilization cycle completes, all the lights 822 can stay turned on, showing a solid lighted ring 820.

FIG. 8A further shows a power PCBA 860. The power PCBA 860 can include at least a light pipe 864 and a power button 862. The light pipe 864 provides cover for the charging light array 213 which is described in FIG. 2B.

The present disclosure also includes a process for sterilizing a surgical loupe. For example, a user can place a loupe on the loupe rest assembly 330, such that the nose bridge of the loupe can rest on the loupe rest assembly arms 333. The user can then bend the loupe rest assembly arms 333 around the loupe to keep the loupe secured. If needed, the user can adjust the loupe rest assembly 330 (move the loupe rest assembly 330 either toward the front of the case, or toward the back) to accommodate varying loupe sizes in the case. The user can also secure the loupe battery to the inner wall 320. The inner wall 320 can be adjusted (moved either toward the front of the case, or toward the back) to fit the battery as desired. A battery clip can be clipped on the top end of the inner wall 320. A battery cable can be wrapped around the cable management assembly 310, for example, using the grooves (or cavities) on the cable management assembly and terminate the male end of battery cable into the female receptacle of cable management assembly 310. If needed, the loupe battery can be plugged into the charging port 335. It should be noted that the steps are not meant to be in a specific order and can be done in different orders. Once all loupe components have been placed into the compartment 300, the lid 101 can be closed. In some embodiments, only after the case 200 has been closed, a sterilization cycle can start. To start a sterilization cycle, the user can activate (pushed) the activation button 210.

It should also be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

To the extent the embodiments disclosed herein include or operate in association with memory, storage, and/or computer readable media, then that memory, storage, and/or computer readable media are non-transitory. Accordingly, to the extent that memory, storage, and/or computer readable media are covered by one or more claims, then that memory, storage, and/or computer readable media is only non-transitory.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

What is claimed:

1. A case for sterilizing and protecting a medical loupe, comprising:

a crush-resistant housing having an upper portion and a lower portion, wherein the upper portion and the lower portion are joined when the housing is in the closed position;

the lower portion further comprising a compartment, the compartment comprises:

one or more array of UV-C light emitting diodes, a battery power source electrically coupled to a plurality of UV-C light emitting diodes, a loupe rest assembly, a cable management assembly, and an inner wall assembly;

a hinge assembly for joining the upper portion and the lower portion; and a safety mechanism for allowing the battery source to power the array of UV-C light emitting diodes only when the housing is in the closed position, wherein a first reflective fabric includes one or more opening sized to receive one or more first transparent covers to cover the plurality of UV-C light emitting diodes.

2. The case of claim 1, wherein the loupe rest assembly is sized to receive the medical loupe.

3. The case of claim 2, wherein the loupe rest assembly includes bendable arms.

4. The case of claim 2, wherein a loupe rest of the loupe rest assembly is operable to securely hold the medical loupe.

5. The case of claim 1, wherein the cable management assembly includes one or more grooves and a female receptacle positioned on a top end of the cable management assembly.

6. The case of claim 1, wherein a bottom end of each of the loupe rest assembly, the cable management assembly, and the inner wall includes one or more extruding studs.

7. The case of claim 6, wherein a bottom surface of the compartment includes one or more slots sized to receive the one or more extruding studs of each of the loupe rest assembly, the cable management assembly, and the inner wall.

8. The case of claim 1, wherein the compartment further comprises a USB-C charging port.

9. The case of claim 1, wherein a bottom portion includes the first reflective fabric configured to separate one or more first components.

10. The case of claim 9, wherein the one or more first components include at least one of one or more battery, a LED PCBA, and a front LED PCB.

11. The case of claim 1, wherein a top portion includes a second reflective fabric configured to separate one or more first components.

12. The case of claim 11, wherein the one or more second components include at least one of a LED PCBA, one or more LED lights, and a light ring cover.

13. The case of claim 12, wherein the second reflective fabric includes one or more opening sized to receive one or more second transparent covers to cover the plurality of UV-C light emitting diodes.

14. The case of claim 1, wherein the top portion includes a user interface button operable to activate a sterilization cycle.

15. The case of claim 1, wherein the top portion includes a light ring operable to indicates a sterilization cycle is in process or has completed.

16. A process for sterilizing a medical loupe in a case for sterilizing and protecting medical loupe, comprising:

placing the medical loupe in a loupe rest assembly;

bending a plurality of arms of the loupe rest assembly to securely hold the medical loupe;

securing a loupe battery to an inner wall;

securing a battery cable to a cable management assembly;

adjusting a position of the cable management assembly;

closing a lid of the case; and activating a sterilization cycle.

17. The process of claim 16 further comprising:

adjusting a position of the loupe rest assembly.

18. The process of claim 16 further comprising:

adjusting a position of the inner wall.

19. The process of claim 16 further comprising:

wrapping the battery cable around the cable management assembly and terminating a male end of the battery cable into a female receptacle of cable management assembly.

* * * * *